United States Patent

Répasi

[11] Patent Number: 5,137,834
[45] Date of Patent: Aug. 11, 1992

[54] PROCESS FOR SELECTIVE COMPLEXOMETRIC ANALYSIS OF N-PHOSPHOROMETHYL-GLYCINE, N-CARBOXYMETHYL-N-PHOSPHONOMETHYL-GLYCINE AND N,N-BISPHOSPHONO-METHYL-GLYCINE

[75] Inventor: János Répasi, Tiszavasvári, Hungary
[73] Assignee: Alkaloida Vegyeszeti Gyar, Tiszavasvári, Hungary
[21] Appl. No.: 508,114
[22] Filed: Apr. 11, 1990
[30] Foreign Application Priority Data
Apr. 11, 1989 [HU] Hungary ............... 1724/89
[51] Int. Cl.$^5$ .......................... G01N 33/00
[52] U.S. Cl. ................... 436/104; 436/163; 436/464; 71/86
[58] Field of Search ........ 436/104, 163, 164; 71/86

[56] References Cited

U.S. PATENT DOCUMENTS

| | | | |
|---|---|---|---|
| 3,799,758 | 3/1974 | Franz | 71/66 |
| 4,130,412 | 12/1978 | Franz | 71/86 |
| 4,131,448 | 12/1978 | Franz | 71/86 |
| 4,486,359 | 12/1984 | Bredel neé0 Hajnóczki et al. | 562/17 |

Primary Examiner—Robert J. Warden
Assistant Examiner—Laura E. Collins
Attorney, Agent, or Firm—Michael N. Meller

[57] ABSTRACT

A process is provided for the quantitative selective complexometric analysis of a sample. First and second aliquot parts of a sample containing N-phosphonomethyl-glycine, N-carboxymethyl-N-phosphonomethyl-glycine or N,N-bis-phosphonomethyl-glycine; or N-phosphonomethyl-glycine and N,N-bis-phosphonomethyl-glycine; or N-phosphonomethyl-glycine and N-carboxymethyl-N-phosphonomethyl-glycine are taken. The first aliquot part is titrated with a bismuth volumetric solution at a Ph=1.8-2.5 in the presence of a methylethymol blue indicator. The second aliquot part is titrated with a copper volumetric solution at a Ph=8-10 in the presence of a murexide indicator. Two end point values are obtained and compared. The difference between these two values result in the determination of the content of N-phosphonomethyl-glycine in the sample.

1 Claim, No Drawings

PROCESS FOR SELECTIVE COMPLEXOMETRIC ANALYSIS OF N-PHOSPHOROMETHYL-GLYCINE, N-CARBOXYMETHYL-N-PHOSPHONOMETHYL-GLYCINE AND N,N-BISPHOSPHONO-METHYL-GLYCINE

The invention relates to a process for selective complexometric analysis of N-phosphonomethyl-glycine, N-carboxymethyl-N-phosphonomethyl-glycine and N,N-bis-phosphonomethyle-glycine.

The N-phosphonomethyl-glycine is a herbicide having a wide effective range. It was put onto the market by the MONSANTO Company under the generic name Glyphosate in 1971. In the past years its advantangeous characteristics have proved themselves. Its salts formed with alkaline metals and aliphatic amines can be dissolved very well in water. In practice it turned out to be non-toxic (its oral $LD_{50}$ value on rats turned out to be 4300 mg/kg). In the event it is used as intended then there is no need for any waiting period as far as its user safety or food safety properties are concerned. It has a very long effective time. When spraying during the autumn one could obtain a weed free time lasting up to 6–8 months. Against most lawn type grasses it is effective in an amount of 1–4 kg/ha, while against annual weeds it is effective in an amount of 0.5–1 kg/ha. It is an environmental safe compound. It becomes bound in the ground very quickly and through a microbiological decomposition it turns into natural materials (carbon dioxide, ammonia, phosphates).

Due to its number of advantages, there is an increasing demand for it from year to year and nowadays it is the most widely used herbicide throughout the world.

Its manufacturing processes are protected by several patents. From such processes the industry, in practice, is using two basic methods the reaction process of which is illustrated on the attached flow sheet.

In the process (a) it is very important to monitor the reaction. In the event that the reaction is stopped prematurely, then a significant amount of CPG will be left in the end product. On the other hand, if the process is stopped too late, then one may expect a further decomposition of PG into aminomethyl-phosphonic acid.

In the process according (b) one has to strictly observe the parameters of the condensation. Otherwise, the illustrated side reaction will accelerate and too much bis-PG will appear. Such a compound is useful on its own as an agent increasing the sugar content and is being used commercially (Polaris, Monsanto).

For this reason, therefore, it is desirable to analyze the produced, technical and formed bis-PG.

For the analysis of PG, CPG, and bis-PG several methods are known. For the analysis of the oxidation mixture of the PG many authors recommend NMR spectroscopic method which, of course, cannot be employed as a routine procedure.

After being nitrosated in an acidic medium, the PG which reacts as a secondary amine, can be well measured by UV absorption determination. (Young, J. C., Khan, S. U.: J. Environ. Sci. Health B 13(i), 59, 1979), or with the help of polarography (Bronstad, J. O., Friestad, H. O.: Analyst 101. 820. 1976).

For the determination of the PG E Kstrom and Johanson employed an amino acid analyser. In a ninhydrin reaction with this method we cannot obtain information about the CPG or bis-PG contents of the samples.

In the event of clean materials, one may employ a potentiometric titrating method, in which case from the proportions of the potentiometric steps deviating from one, one may draw conclusions about the CPG or bis-PG contents of the PG. It appears, however, that such approach may lead to false results about the reaction mixture or about a technical product.

Gas chromatographic determinations or analysis are made difficult by the fact that neither one of the PG, CPG or the bis-PG is volatile. This problem can be eliminated by derivative formation (trifluoroacetylation and diazomethane methylation); however, the process in this way becomes very cumbersome, lengthy and it is worth only to use for the residue analysis.

HPLC analysis has been also discussed by many authors (Lundgren, J. N.: J. Agric. Food. Chem., 34, 535,( 1986); Archer, T. E. et al., J. Agric Food. Chem., 32. 586, (1984)). Here the difficulty arises due to the very weak UV absorption of the compounds. The derivative formation prior to or after the column can be resolved; however, even in this case the methods discussed in connection with gas chromatography will still hold.

Known is also an analysis of the reaction mixtures by capillary isotachophoresis (Krivankova, K., Bocek, P.: Electrophoresis: Weinheim, FRG., 7(2), 100, (1986)) which again cannot be called routine. Considering the above, it seemed desirable to develop a selective process for the determination of PG, CPG and bis-PG which is simple in its realization, inexpensive to use, and reliable.

The complex forming properties of the above-mentioned compounds have been discussed by many authors.

Schwarzenbach and his associates (Helv. Chim. Acta, 32, 1175, (1949)) compared with various derivatives of iminodiacetic acids and reported several stability constants of the metallic ion-CPG.

Martel and Ockerbloom (J. Am. Chem. Soc., 80, 2351, (1958)) reported also a possible structure for the complexes.

Fiedelman (U.S. Pat. No. 3,385,675) used the very bad solubility of the CPG-Calcium complex for the elimination of the calcium from the sodium chloride.

Shopron and Sirkij (Koord. Khim. 2., 1082, (1976)) analyzed the electron distribution of the CPG-Complexes.

Hayashida (Japanese Patent Appln. 71-216047) accomplished the retention of the zinc solution in an alkaline zinc galvanizing bath.

The complex forming character of the PG is underlined by the fact that the herbicide activity is reduced in the presence of iron and calcium ions and such reduction can be eliminated by the addition of EDTA (Anonym.: Res. Discl .148 , 10, (1976)).

Many others treated the determination of the stability constants. A few characteristic values (Log $K_{ST}$) are summarized in the following table:

TABLE 1

|    | PG   | bis-PG | CPG  |
|----|------|--------|------|
| Mo | 3.3  | 4.2    | 6.0  |
| Ca | 3.2  | 3.8    | 7.1  |
| Mn | 5.5  | 6.3    | 8.0  |
| Zn | 8.7  | 9.0    | —    |
| Cu | 11.9 | 12.8   | 12.5 |

The above developments gave us the idea to entertain the possibility of performing a quantitative complexometric analysis. During our experiments we came to the realization that in the case of an appropriate metallic ion-indicator-pH system the PG and CPG or the PG and bis-PG can be selectively measured while being jointly present.

The considerable advantage of such processes resides in that it can be performed in an inexpensive fashion, it does not require major instrumentation, it needs only a few simple chemical reagents and the glassware is that commonly used in laboratories. As a result, the process can be employed in such areas where analytical control would not be possible. It will also open the possibility that a customer will be able to simply control the effectiveness of the produced agent, or if necessary, the concentration of the spraying solution can be determined.

The speediness of the process makes it also adaptable to follow the reaction which is specially important when PG is manufactured from CPG.

The process is performed in such a manner that an appropriate quantity of a sample is titrated with a copper volumetric solution at a pH value of 8–10 and in the presence of a murexide indicator, to a color of yellowish-green, that is, the PG-bis-PG content is calculated in a known manner, then another appropriate quantity of the sample becomes titrated with a bismuth volumetric solution at a pH value of 1.5–2.5 in the presence of a methylthymol blue indicator to a color of bluish-purple, i.e., the CPG or bis-PG content will be calculated in a known manner. The difference between the two measurements will give the PG content.

EXAMPLE

1. Preparation of the Copper Volumetric Solution 3.6 g. of copper (II) sulfate pentahydrate is put into a 1 liter flask and dissolved in distilled water, then the volume of the solution will be increased to 1 liter (approximately 0.015 mol/l ).

2. Determination of the Strength of the Copper Volumetric Solution 10.0 ml of a 0.01 mol/l EDTA solution is introduced with a pipette into a titrating flask, then 100 ml water, 1 ml of 1 mol/l NaOH solution, 10 ml of 50 g/l ammonium chloride solution and a pinch of murexide indicator mixture on the tip of a spatula (1 g. murexide compound well mixed with 300 g. of potassium nitrate) is added thereto. The solution becomes titrated with the copper volumetric solution to a yellowish-green color. The average of three measurements will give the mean consumption (V).

The f value of the copper volumetric solution:

$$f_1 = \frac{10 \times 0.01 \times f}{V \times 0.015}$$

where f is the f value of the EDTA solution.

3. Preparation of the Bismuth Volumetric Solution:

4.36 g. of basic bismuth nitrate [4 BiNO$_3$(OH)$_2$·×BiOH] is dissolved in 10 ml of 68 w/w % nitric acid and in a small amount of water. Then the volume of the solution is increased by the addition of water acidified with 5 ml of 68 w/w % nitric acid to a volume of 1 liter (approximately 0.015 mol/l ).

4. Determination of the Strength of the Bismuth Volumetric Solution 10.0 ml of a 0.01 mol/l EDTA solution is introduced by pipette into a titrating flask, then 30–40 ml of water, 0.5 ml of a 10 w/w % nitric acid and a pinch of mixed methylthymol blue indicator is added thereto on the tip of a spatula (1 g. methylthymol blue compound well mixed with 100 g of potassium nitrate). The solution will be titrated with the bismuth volumetric solution to a bluish-purple color. The average result of three measurements will give the mean consumption.

The f value of the bismuth volumetric solution:

$$f_2 = \frac{10 \times 0.01 \times f}{V \times 0.015}$$

that f is the f value of the EDTA solution.

5. Analysis of the Technical PG

A 200–300 mg quantity of the sample which has been dried to consent weight consistency is put into with an analytical accuracy and dissolved with a small amount of water and 2 ml of 1 mol/l sodium-hydroxide. Then the volumetric flask, which has a volume of 100 ml, is filled with distilled water up to the mark.

A 10 ml portion of the solution is introduced into a titrating flask with pipette and 100 ml water, 1 ml of a 1 mol/l sodium hydroxide, 10 ml of a 50 g/l ammonium chloride, as well as a pinch of murexide indicator on the tip of a spatula added thereto. The solution is titrated with a copper volumetric solution to a yellowish-green color. From the average three measurements, the mean consumption $V_1$ is calculated. A 50 ml portion of the previously prepared stock solution is introduced into the titrating flasks with pipettes. 1 ml of 10% nitric acid and a pinch of methylthymol blue indicator on the tip of a spatula is introduced thereto. The bismuth volumetric solution having a yellow color and obtained in such a manner is titrated to a bluish-purple color. From the three measurements, the mean consumption ($V_2$) is calcula .

In the following table, the analysis of five samples is summarized.

Now in this case, due to the technological conditions, one may expect some impurities of bis-PG (MW=263.1).

The factor of the cuprous measuring solution: $f_1 = 1.0291$.

The factor of the bismuth measuring solution is: $f_2 = 1.0032$.

TABLE II

| Sample (mg) | $V_1$ (ml) | $V_2$ (ml) | $f_1 \times V_1 - \frac{f_2 \times V_2}{5}$ | bis-PG (w/w %) | PG (w/w %) |
|---|---|---|---|---|---|
| 237.0 | 8.85 | 0.40 | 9.03 | 1.3 | 96.6 |
| 252.3 | 9.42 | 0.62 | 9.57 | 1.9 | 96.2 |
| 225.3 | 8.53 | 0.58 | 8.66 | 2.0 | 97.5 |
| 241.5 | 9.18 | 0.51 | 9.34 | 1.7 | 98.1 |
| 213.4 | 9.05 | 0.44 | 8.20 | 1.6 | 97.4 |

6. Analysis of the Mixture PG and CPG

From standard PG (MW=169.1) and CPG (MW=227.1) mixtures are prepared and proceed according to Example 5.

TABLE III

| Sample (mg) | Calculated CPG w/w % | $V_1$ (ml) | $V_2$ (ml) | $f_1 \times V_1 - \dfrac{f_2 \times V_2}{5}$ | | Measured CPG w/w % | Measured PG w/w % |
|---|---|---|---|---|---|---|---|
| 243.5 | 1.0 | 9.29 | 0.34 | | 9.49 | 0.95 | 98.86 |
| 223.7 | 2.0 | 8.53 | 0.64 | | 8.65 | 1.96 | 98.08 |
| 232.4 | 5.0 | 8.79 | 1.76 | | 8.69 | 5.17 | 94.85 |
| 219.9 | 10.0 | 8.15 | 3.24 | | 7.74 | 10.11 | 89.69 |
| 236.1 | 20.0 | 8.62 | 7.00 | | 7.47 | 20.26 | 80.25 |

7. Following the Oxidation of the CPG

From the oxidation mixture samples are collected from time to time, and filtered through a filter paper and are titrated in appropriate quantities. We proceed similarly as in Example 5, with the additional comment that the volumes of the titrating solutions are set with distilled water which, in the case of the copper volumetric solution, is approximately 100 ml, and in the case of the bismuth volumetric solution is approximately 50 ml. If we are titrating only with bismuth, then we can follow only the reduction of the CPG, on the other hand, when we titrate with copper than the formation of PG can also be observed. The decreasing of the sum of PG and CPG indicates the occurrence of side reactions. In our Example 3 illustrate the results of the following of the reactions at constant quantities of samples

TABLE IV

| Oxidation time hrs. | $f_2 \times V_1$ ml | $f_2 \times V_2$ ml | CPG mol % | PG mol % | CPG + PG mol % |
|---|---|---|---|---|---|
| 0. | 15.1 | 15.1 | 100.0 | 0.0 | 100.0 |
| 0.5 | 15.0 | 12.9 | 85.4 | 13.9 | 99.3 |
| 1.0 | 14.9 | 10.8 | 71.5 | 27.2 | 98.7 |
| 1.5 | 14.9 | 8.6 | 57.0 | 41.7 | 98.7 |
| 2.0 | 14.7 | 6.6 | 43.7 | 53.6 | 97.3 |
| 2.5 | 14.5 | 4.5 | 29.8 | 66.2 | 96.0 |
| 3.0 | 14.4 | 2.4 | 15.9 | 79.5 | 95.4 |
| 3.5 | 14.1 | 0.3 | 2.0 | 91.4 | 93.4 |

8. Analysis of Herbicide Solution Containing 200 g/l PG-Sodium 10.0 ml from the material is introduced by pipette into a 1 l volumetric flask and filled up with distilled water up to the mark. From this stock solution according to the discussion of example 5 the PG and, depending on the technology, the CPG or bis-PG is determined.

In the tables, next following, the results of five are illustrated and for comparison the data obtained from the Nitrosation method is also given.

TABLE V

| Sample | bis-PG (g/l) | PG/Complexometry (g/l) | PG nitrosation (g/l) |
|---|---|---|---|
| 1 | 3.2 | 198.2 | 202.7 |
| 2 | 2.8 | 203.4 | 200.1 |
| 3 | 3.6 | 201.7 | 203.9 |
| 4 | 3.1 | 197.9 | 195.0 |
| 5 | 2.4 | 201.3 | 199.5 |

9. Analysis of the Technical CPG and bis-PG

From the sample which has been dried to a constant weight consistency; a quantity of 250 or 300 mg is accurately measured out and put into the flask and then dissolved in a small amount of water and in a 2 ml solution of a 1 mol/l sodium hydroxide, then in the volumetric flask having a volume of 100 ml filled with distilled water up to the mark. A 10 ml portion from the such obtained stock solution is introduced into a titrating flask with pipette, then approximately 40 ml distilled water is added thereto as well as 1 ml of a 10 w/w % nitric acid and a pinch of methylthymol blue mixture indicator on the tip of a spatula, then with a bismuth volumetric solution it is titrated to a bluish-purple color. From the consumption the CPG or bis-PG content is calculated according to the known manner.

In the following table the data calculated from the five parallel titrations of each sample is given.

TABLE VI

| Sample | CPG w/w % | Sample | bis-PG w/w % |
|---|---|---|---|
| 1 | 98.2 | 6 | 97.7 |
| 2 | 98.7 | 7 | 98.5 |
| 3 | 98.6 | 8 | 98.3 |
| 4 | 98.0 | 9 | 98.1 |
| 5 | 98.4 | 10 | 98.7 |

10. Analysis of Regulator Solution Containing 85 w/w % bis-PG

From the sample 400 mg quantity is accurately measured out and we proceed with it according to example 9. The effective content of the five samples is given below.

TABLE VII

| | Sample | | | | |
|---|---|---|---|---|---|
| | 1 | 2 | 3 | 4 | 5 |
| bis-PG (w/w %) | 85.2 | 87.1 | 88.3 | 86.4 | 86.6 | a. 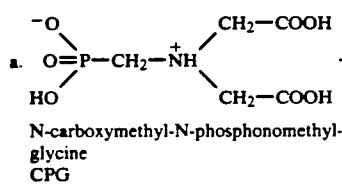 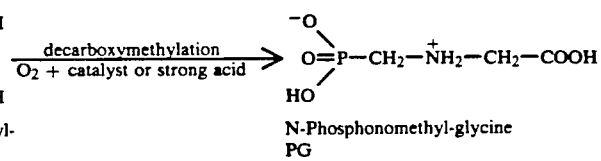

N-carboxymethyl-N-phosphonomethyl-glycine
CPG

N-Phosphonomethyl-glycine
PG

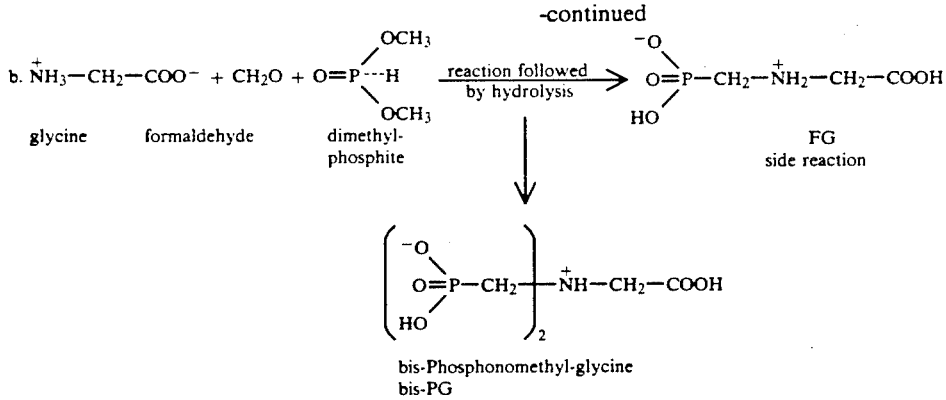

bis-Phosphonomethyl-glycine
bis-PG

I claim:
1. A process for the quantitative selective complexometric analysis of a sample which comprises
 a) providing a sample which contains N-phosphonomethyl-glycine, N-carboxymethyl-N-phosphonomethyl-glycine or N,N-bis-phosphonomethyl-glycine; or N-phosphonomethyl-glycine and N,N-bis-phosphonomethyl-glycine; or N-phosphonomethyl-glycine and N-carboxymethyl-N-phosphonomethyl-glycine:
 b) providing first and second aliquot parts of said sample;
 c) titrating to an end point the first aliquot part with a bismuth volumetric solution at pH=1.8-2.5 in the presence of a methylethymol blue indicator,
 d) titrating to an end point the second aliquot part with a copper volumetric solution at a pH=8-10 in the presence of a murexide indicator, and
 e) comparing the two end point values and determining the content in the sample of N-phosphonomethyl-glycine by the difference in these two values.

* * * * *